United States Patent
Gawel, Jr.

[11] Patent Number: 5,970,643
[45] Date of Patent: Oct. 26, 1999

[54] APPARATUS TO ENHANCE THE USE OF SCENTS

[76] Inventor: Joseph W. Gawel, Jr., 26 New Preston Hill Rd., New Preston, Conn. 06777

[21] Appl. No.: 09/131,357

[22] Filed: Aug. 10, 1998

[51] Int. Cl.[6] .......................... A01M 27/00; A24F 25/00
[52] U.S. Cl. .................................. 43/1; 239/51.5
[58] Field of Search ................... 43/1; 239/51.5, 239/55, 57; 261/26, 30; 422/125, 124, 123

[56] References Cited

U.S. PATENT DOCUMENTS

| | | | |
|---|---|---|---|
| Re. 33,864 | 3/1992 | Steiner et al. | 261/30 |
| 1,655,248 | 1/1928 | Sharp | 261/30 |
| 2,610,893 | 9/1952 | Collins et al. | 239/51.5 |
| 2,662,332 | 12/1953 | McIntire | 43/129 |
| 2,796,290 | 6/1957 | Downs | 239/55 |
| 3,257,077 | 6/1966 | Corning | 239/47 |
| 3,747,902 | 7/1973 | Bailey | 261/30 |
| 3,790,081 | 2/1974 | Thornton et al. | 239/55 |
| 3,993,444 | 11/1976 | Brown | 239/57 |
| 4,301,095 | 11/1981 | Mettler et al. | 261/30 |
| 4,377,399 | 3/1983 | Bryson | 239/57 |
| 4,666,638 | 5/1987 | Baker et al. | 261/26 |
| 4,695,435 | 9/1987 | Spector | 422/124 |
| 4,743,406 | 5/1988 | Steiner et al. | 261/30 |
| 4,788,787 | 12/1988 | Konietzki | 43/1 |
| 4,808,347 | 2/1989 | Dawn | 261/30 |
| 4,830,791 | 5/1989 | Muderlak et al. | 261/26 |
| 4,931,224 | 6/1990 | Holzner, Sr. | 261/30 |
| 4,931,258 | 6/1990 | Zlotnik et al. | 422/124 |
| 5,230,867 | 7/1993 | Kunze et al. | 422/123 |
| 5,250,265 | 10/1993 | Kawaguchi et al. | 422/107 |
| 5,305,541 | 4/1994 | Simpson | 43/1 |
| 5,307,584 | 5/1994 | Jarvis | 43/1 |
| 5,342,584 | 8/1994 | Fritz et al. | 422/124 |
| 5,422,078 | 6/1995 | Colon | 422/123 |
| 5,876,678 | 3/1999 | Harrell et al. | 422/125 |

*Primary Examiner*—Michael J. Carone
*Assistant Examiner*—Fredrick T. French, III

[57] ABSTRACT

An apparatus to enhance the use of scents including a housing which has an interior surface and an external surface. The housing also has an input end and an output end and downwardly extending legs. A fan is provided with a drive shaft. The fan is located within the housing adjacent to the output end. A foam padding is provided and is located adjacent to the inlet end of the housing to hold the fan during operation and use. A source of potential is provided with an associated line coupled to the fan motor and with an off/on switch to selectively energize and de-energize the power source and the fan. Lastly, a radial aperture is formed in the upper extent of the housing in proximity to the output end and a liquid-retaining sponge member has a quantity of animal-attracting fluid therein and a line having an upper end extending through, and supporting within. The aperture and a lower end support the sponge member adjacent to the output end of the housing in proximity to the axis whereby when the switch is activated to power the fan. A flow of air is directed over the sponge member and liquid therein for generating an odor to attract animals for being hunted.

5 Claims, 2 Drawing Sheets

APPARATUS TO ENHANCE THE USE OF SCENTS

BACKGROUND OF THE INVENTION

1. Field of the Invention

The present invention relates to an apparatus to enhance the use of scents and more particularly pertains to disseminating an animal-attracting odor to enhance hunting.

2. Description of the Prior Art

The use of hunting aids of known designs and configurations is known in the prior art. More specifically, hunting aids of known designs and configurations heretofore devised and utilized for the purpose of improving hunting techniques through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,307,584 to Jarvis, issued May 3, 1994 discloses a deer scent dispenser and method. U.S. Pat. No. 5,305,541 to Simpson, issued Apr. 26, 1994 discloses a game scent dispensing apparatus. U.S. Pat. No. 4,808,347 to Dawn, issued Feb. 28, 1989 discloses a fan driven air freshener. U.S. Pat. No. 3,257,077 to Corning, issued Jun. 21, 1966 discloses a wick-type deodorizer and attachment means. U.S. Pat. No. 2,662,332 to McIntire, issued Dec. 15, 1953 discloses an insecticide fogger. Lastly, foreign patent numbers EP 0462 605 A2 to Orson, Issue/Priority Date Jun. 19, 1991 discloses a fragrance dispensing composition with controlled evaporation rate and air fragrance dispenser for dispensing same and WO 96/03218 to Hart et al., Issue/Priority Date Feb. 8, 1996 discloses an apparatus for providing bursts of spray of a fluid.

While these devices fulfill their respective, particular objectives and requirements, the aforementioned patents do not describe apparatus to enhance the use of scents as described herein.

In this respect, the apparatus to enhance the use of scents according to the present invention substantially departs from the conventional concepts and designs of the prior art, and in doing so provides an apparatus primarily developed for the purpose of disseminating an animal-attracting odor to enhance hunting.

Therefore, it can be appreciated that there exists a continuing need for a new and improved apparatus to enhance the use of scents which can be used for disseminating an animal-attracting odor to enhance hunting. In this regard, the present invention substantially fulfills this need.

SUMMARY OF THE INVENTION

In view of the foregoing disadvantages inherent in the known types of hunting aids of known designs and configurations now present in the prior art, the present invention provides an improved apparatus to enhance the use of scents. As such, the general purpose of the present invention, which will be described subsequently in greater detail, is to provide a new and improved apparatus to enhance the use of scents and method which has all the advantages of the prior art and none of the disadvantages.

To attain this, the present invention essentially comprises a new and improved odor device system 10 for enhancing the use of scents including a housing in a generally cylindrical configuration with a central horizontal axis therethrough. The housing has an interior cylindrical surface and an external cylindrical surface. The housing has an input end and an output end. The housing also has downwardly extending legs in an arcuate configuration. A fan is provided with a drive shaft with a plurality of blades rotatable about a central horizontal axis coincident with the central horizontal axis of the housing. The fan is located within the housing adjacent to the output end. The fan is supported in a generally rectilinear frame. Also provided is a foam padding having a cylindrical exterior surface in supporting contact with the interior surface of the housing and with a generally rectilinear interior surface receiving and supporting the exterior surface of the frame. The foam is located adjacent to the inlet end of the housing to hold the fan during operation and use. Also provided is a source of potential including batteries secured to the undersurface of the legs at a central extent thereof with an associated line coupled to the fan motor and with an off/on switch 48 to selectively energize and de-energize the power source and the fan. Lastly provided is a radial aperture formed in the upper extent of the housing in proximity to the output end and a liquid-retaining sponge member having a quantity of animal-attracting fluid therein and a line having an upper end extending through, and supporting within, the aperture and a lower end supporting the sponge member adjacent to the output end of the housing in proximity to the axis whereby when the switch is activated to power the fan, a flow of air will be directed over the sponge member and liquid therein for generating an odor to attract animals for being hunted.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved apparatus to enhance the use of scents which has all of the advantages of the prior art hunting aids of known designs and configurations and none of the disadvantages.

It is another object of the present invention to provide a new and improved apparatus to enhance the use of scents which may be easily and efficiently manufactured and marketed.

It is further object of the present invention to provide a new and improved apparatus to enhance the use of scents which is of durable and reliable constructions.

An even further object of the present invention is to provide a new and improved apparatus to enhance the use of scents which is susceptible of a low cost of manufacture with regard to both materials and labor, and which accordingly is then susceptible of low prices of sale to the consuming public, thereby making such apparatus to enhance the use of scents economically available to the buying public.

Even still another object of the present invention is to provide an apparatus to enhance the use of scents for disseminating an animal-attracting odor to enhance hunting.

Lastly, it is an object of the present invention to provide a new and improved apparatus to enhance the use of scents that includes a housing which has an interior surface and an external surface. The housing also has an input end and an output end and downwardly extending legs. A fan is provided with a drive shaft. The fan is located within the housing adjacent to the output end. A foam padding is provided and is located adjacent to the inlet end of the housing to hold the fan during operation and use. A source of potential is provided with an associated line coupled to the fan motor and with an off/on switch to selectively energize and de-energize the power source and the fan. Lastly, a radial aperture is formed in the upper extent of the housing in proximity to the output end and a liquid-retaining sponge member has a quantity of animal-attracting fluid therein and a line having an upper end extending through, and supporting within. The aperture and a lower end support the sponge member adjacent to the output end of the housing in proximity to the axis whereby when the switch is activated to power the fan. A flow of air is directed over the sponge member and liquid therein for generating an odor to attract animals for being hunted.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
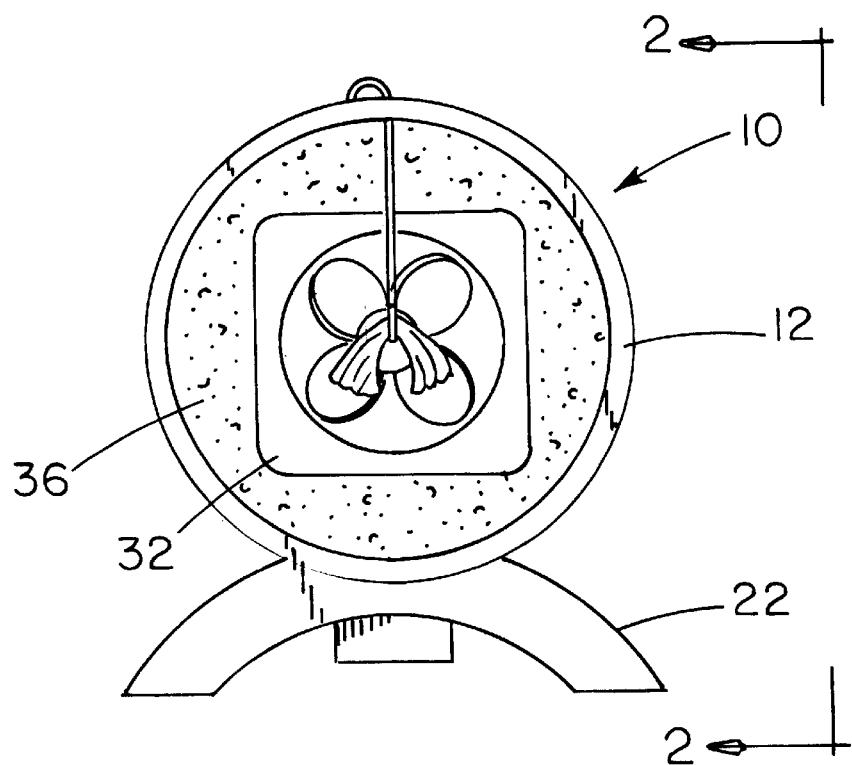
FIG. 1 is a front elevational view of the preferred embodiment of the apparatus to enhance the use of scents constructed in accordance with the principles of the present invention.
Figure 2:
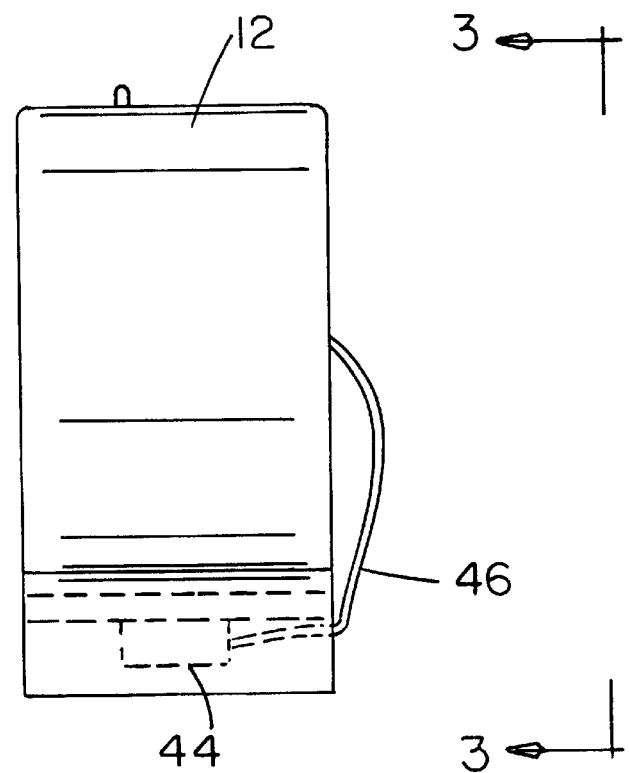
FIG. 2 is a side elevational view of the apparatus shown in FIG. 1 taken at line 2—2 of FIG. 1.
Figure 3:
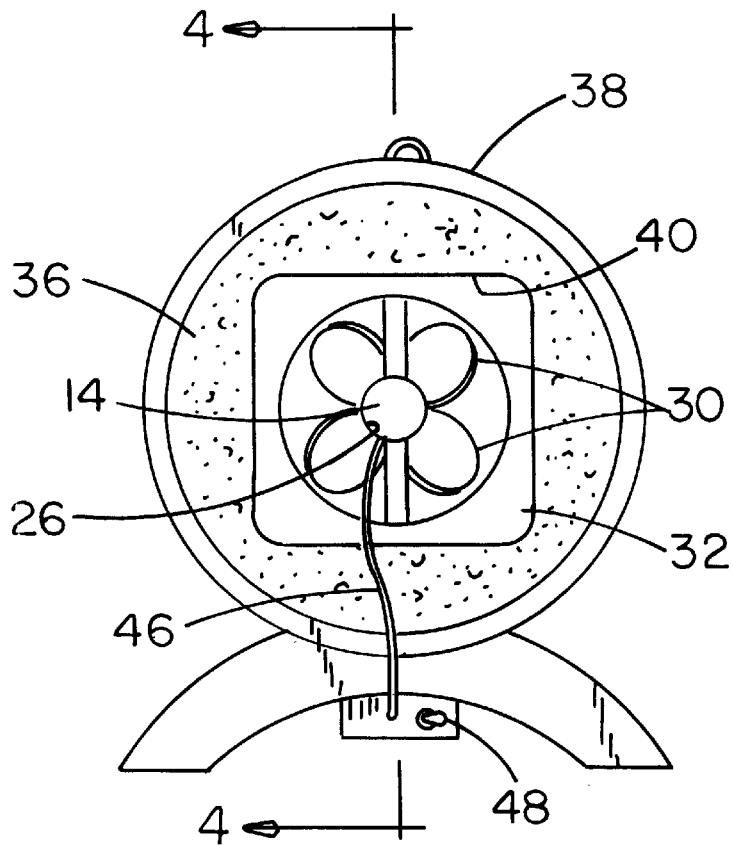
FIG. 3 is a rear elevational view of the apparatus shown in FIGS. 1 and 2 taken at line 3—3 of FIG. 2.
Figure 4:
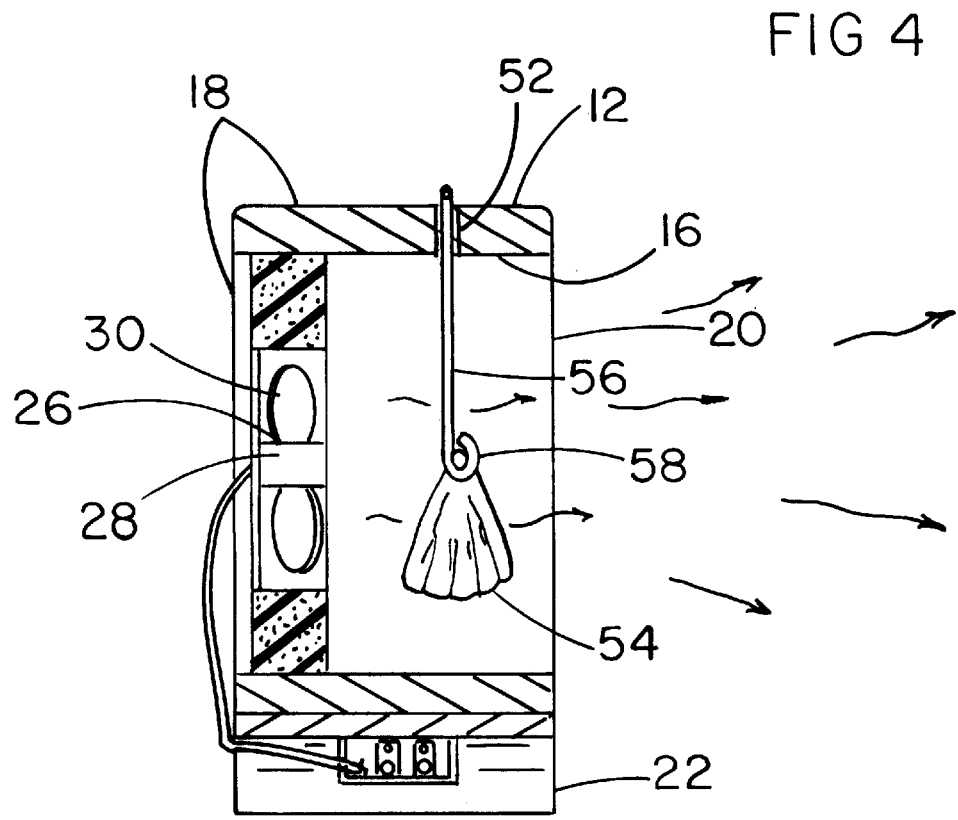
FIG. 4 is a cross-sectional view taken along line 4—4 of FIG. 3.

With reference now to the drawings, and in particular to FIG. 1 thereof, the preferred embodiment of the new and improved apparatus to enhance the use of scents embodying the principles and concepts of the present invention and generally designated by the reference numeral 10 will be described.

The present invention, the apparatus to enhance the use of scents 10, is comprised of a plurality of components. Such components in their broadest context include a housing, a fan and a source of potential. Such components are individually configured and correlated with respect to each other so as to attain the desired objective.

The new and improved odor device system 10 for enhancing the use of scents comprises, a housing 12 in a generally cylindrical configuration with a central horizontal axis 14 therethrough. The housing has an interior cylindrical surface 16 and an external cylindrical surface 18. The housing has an input end 18 and an output end 20. The housing also has downwardly extending legs 22 in an arcuate configuration.

A fan 26 is provided with a drive shaft 28 with a plurality of blades 30 rotatable about a central horizontal axis coincident with the central horizontal axis of the housing. The fan is located within the housing adjacent to the output end. The fan is supported in a generally rectilinear frame 32.

Also provided is a foam padding 36 having a cylindrical exterior surface 38 in supporting contact with the interior surface of the housing and with a generally rectilinear interior surface 40 receiving and supporting the exterior surface of the frame. The foam is located adjacent to the inlet end of the housing to hold the fan during operation and use.

Also provided is a source of potential 44 including batteries secured to the undersurface of the legs at a central extent thereof with an associated line 46 coupled to the fan motor and with an off/on switch 48 to selectively energize and de-energize the power source and the fan.

Lastly provided is a radial aperture 52 formed in the upper extent of the housing in proximity to the output end and a liquid-retaining sponge member 54 having a quantity of animal-attracting fluid therein and a line 56 having an upper end extending through, and supporting within, the aperture and a lower end 58 supporting the sponge member adjacent to the output end of the housing in proximity to the axis whereby when the switch is activated to power the fan, a flow of air will be directed over the sponge member and liquid therein for generating an odor to attract animals for being hunted.

The system of the present invention as described hereinabove is a hunting accessory designed to enhance the use of scents. A small fan is used to force air over and around a scent-soaked pad in order to increase the chance of a deer noticing the scent. The working model consists of an open-ended cylindrical housing within which is mounted a battery-powered 12 V DC fan. Foam rubber is used to hold the fan in place in the housing, and this also serves to dampen vibration.

Positioned in front of the fan is a wire clasp designed for holding a scent-soaked felt pad. The assembly is mounted upon a base comprised of a vertically cut section of pipe creating legs as well as an inverted cavity within which two batteries can be mounted.

The system includes the basic working components of a fan, batteries and felt/bracket. The housing would not be limited to the shape and assembly methods of the working model. A swivel base and/or a hanging device/method might be included. An on/off switch would be featured on the exterior of the housing.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by letters patent of the united states is as follows:

1. An odor device system for enhancing the use of scents comprising, in combination:

a housing in a generally cylindrical configuration with a central horizontal axis therethrough, the housing having an interior cylindrical surface and an external cylindrical surface, the housing having an input end and an output end, the housing also having downwardly extending legs in an arcuate configuration;

a fan having a drive shaft with a plurality of blades rotatable about a central horizontal axis coincident with the central horizontal axis of the housing, the fan being located within the housing adjacent to the output end, the fan being supported in a generally rectilinear frame;

a foam padding having a cylindrical exterior surface in supporting contact with the interior surface of the housing and with a generally rectilinear interior surface receiving and supporting the exterior surface of the frame, the foam being located adjacent to the inlet end of the housing to hold the fan during operation and use;

a source of potential including batteries secured to the undersurface of the legs at a central extent thereof with an associated line coupled to the fan motor and with an off/on switch to selectively energize and de-energize the source of potential and the fan; and a radial aperture formed in the upper extent of the housing in proximity to the output end and a liquid-retaining sponge member having a quantity of animal-attracting fluid therein and a line having an upper end extending through, and supporting within, the aperture and a lower end supporting the sponge member adjacent to the output end of the housing in proximity to the axis whereby when the switch is activated to power the fan, a flow of air will be directed over the sponge member and liquid therein for generating an odor to attract animals for being hunted.

2. An odor device system comprising:

a housing having an interior surface and an external surface, the housing having an input end and an output end, the housing also having downwardly extending legs;

a fan having a drive shaft, the fan being located within the housing adjacent to the output end;

a foam padding, the foam being located adjacent to the inlet end of the housing to hold the fan during operation and use;

a source of potential with an associated line coupled to the fan motor and with an off/on switch to selectively energize and de-energize the source of potential and the fan; and a radial aperture formed in the upper extent of the housing in proximity to the output end and a liquid-retaining sponge member having a quantity of animal-attracting fluid therein and a line having an upper end extending through, and supporting within, the aperture and a lower end supporting the sponge member adjacent to the output end of the housing in proximity to the axis whereby when the switch is activated to power the fan, a flow of air will be directed over the sponge member and liquid therein for generating an odor to attract animals for being hunted.

3. The system as set forth in claim 2 wherein the fan has a drive shaft with a plurality of blades rotatable about an axis coincident with the central axis of the housing, the fan being located within the housing adjacent to the output end.

4. The system as set forth in claim 2 wherein the foam padding has a cylindrical exterior surface in supporting contact with the interior surface of the housing and with a generally rectilinear interior surface receiving and supporting the exterior surface of a frame, the foam being located adjacent to the inlet end of the housing to hold the fan during operation and use.

5. The system as set forth in claim 2 wherein the source of potential includes batteries secured to the undersurface of the legs at a central extent thereof with an associated line coupled to the fan motor and with an off/on switch to selectively energize and de-energize the source of potential and the fan.

* * * * *